United States Patent [19]

Citronowicz

[11] Patent Number: 5,688,265

[45] Date of Patent: Nov. 18, 1997

[54] BATTERY POWERED CAUTERY ASSEMBLY

[75] Inventor: Moshe Citronowicz, St. Petersburg, Fla.

[73] Assignee: Aaron Medical Industries, Inc., St. Petersburg, Fla.

[21] Appl. No.: 521,569

[22] Filed: Aug. 30, 1995

[51] Int. Cl.[6] .................................................. A61B 17/38
[52] U.S. Cl. ............................ 606/30; 219/233; 219/240
[58] Field of Search .................................. 606/29, 30, 42; 219/233, 240; 30/140

[56]  References Cited

U.S. PATENT DOCUMENTS

| | | |
|---|---|---|
| 3,613,682 | 10/1971 | Naylor ........................ 606/30 |
| 3,978,312 | 8/1976 | Barton et al. ................ 606/30 |
| 4,563,570 | 1/1986 | Johns ........................... 606/30 |
| 4,606,342 | 8/1986 | Zamba et al. ................ 606/30 |

*Primary Examiner*—Lee S. Cohen
*Attorney, Agent, or Firm*—A. W. Fisher, III

[57]  ABSTRACT

A battery powered cautery assembly comprising a cautery and a removable safety cover wherein the cautery comprises a substantially cylindrical outer housing having at least one battery disposed in the proximal end thereof, a cautery element attached to the distal end thereof with a conductor disposed to selectively couple the battery to the cautery element and a switch movable between a first and second position hingedly attached thereto and disposed to selectively engage the conductor when in the second position to selectively connect the cautery element to the battery.

23 Claims, 2 Drawing Sheets

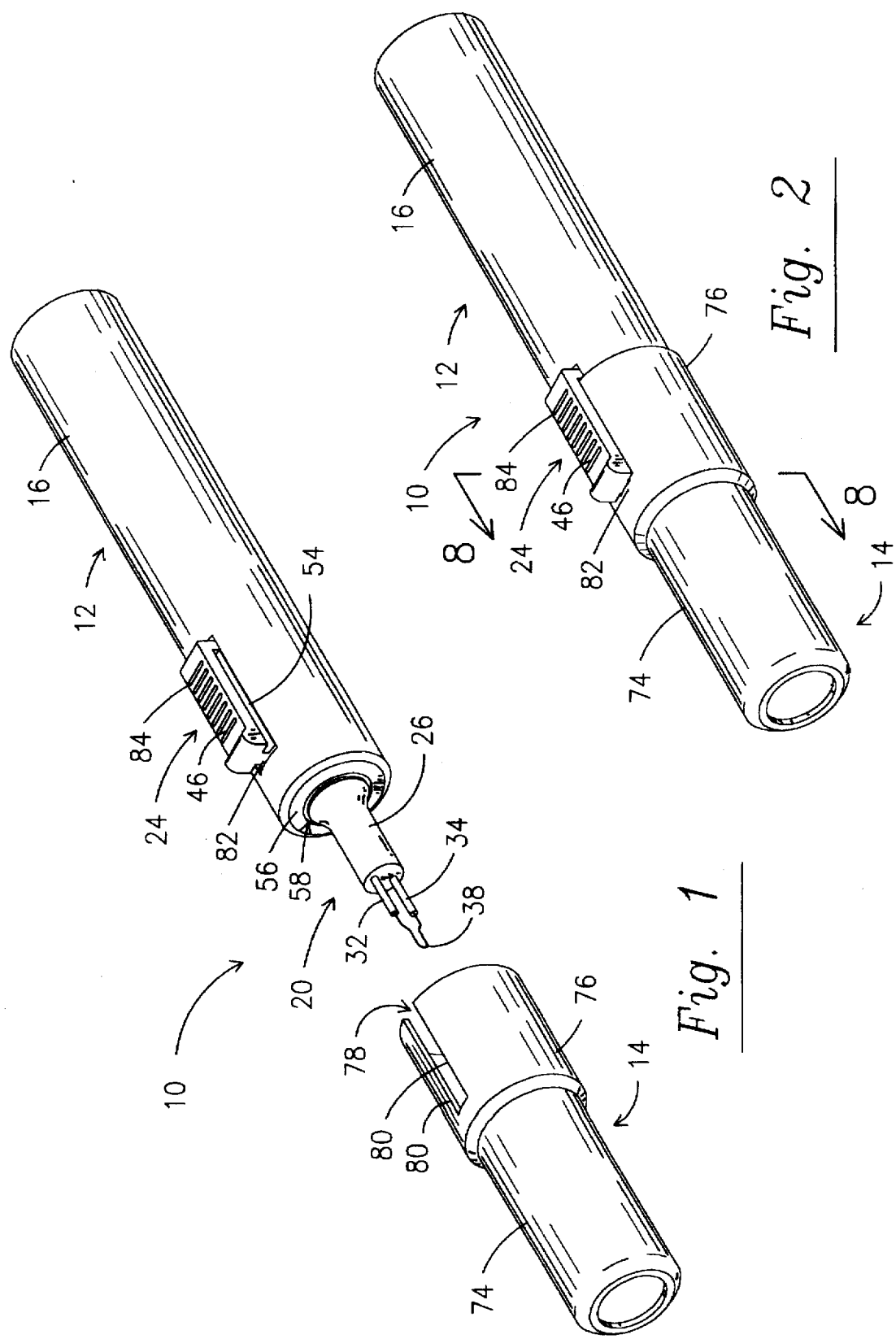

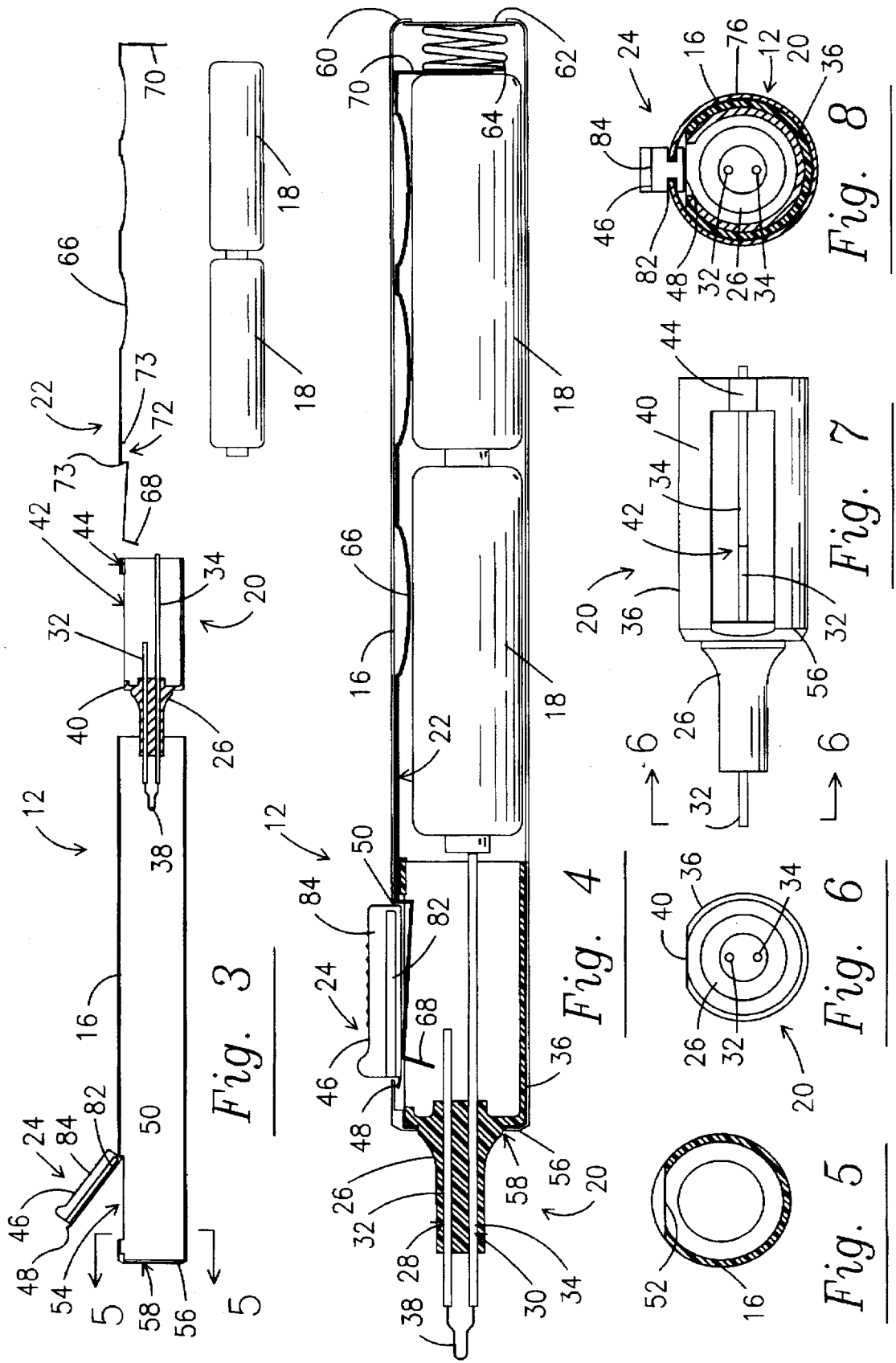

BATTERY POWERED CAUTERY ASSEMBLY

BACKGROUND OF THE INVENTION

1. Field of the Invention

A battery powered cautery assembly comprising a housing having a switch actuator integrally formed therewith.

2. Description of the Prior Art

Numerous pen lights, cauteries and the like comprising a current or voltage source in combination with a light bulb or heating element and switch to selectively actuate the device have been developed for use in the medical field and similar endeavors.

The switch may comprise a plunger type switch similar to those used in mechanical pencils and ball point pens in which the switch is axially aligned with the power source and light bulb or heating element to move the power source into and out of operative engagement with the light bulb heating element itself. Several working parts with attendant manufacturing and assembly the plunger type switch is unfortunately subject to wear and malfunction rendering the device inoperable.

A second type of switching comprises a clip-like member attached to or between the voltage current source and a conductive member operatively coupled to the light bulb or heating element. The clip-like member has a first and second position such that the member may be moved into and out of closed and open circuit configuration. These clip-like members often move to the closed position causing inadvertent current or voltage drain significantly reducing the useful life of the battery or power source.

U.S. Pat. No. 4,563,570 describes a battery powered cautery including a cylindrical housing configured to retain a voltage source and an electrically heated cautery tip carried by the front end of the housing and adapted to be selectively energized from the power source by a manually operable switch on the housing. The switch includes a contact element having rear end connected to a terminal of the power source and a front end movable into and out of engagement with a terminal electrode of the electrically heated tip to make and break the circuit between the tip and the power source by an operation of a depressible switch actuator on housing. A removable safety cover configured to mount on the front of the housing enclosed the switch actuator and heating tip to prevent inadvertent switch actuation and to protect the tip when the cautery is being stored or transported. The safety cover includes an electrical insulating member which projects into the housing to a position between the front end of the movable contact element and the terminal electrode of the tip when the cover is mounted on the housing to mechanically lock the switch actuator against depression and to positively electrically insulate the front end of the contact element from the tip terminal electrode thereby preventing inadvertent energization of the electrically heated tip. A rotatably adjustable variable resistor may be mounted on the rear end of the housing to allow the temperature of the heated tip to be selectively varied.

U.S. Pat. No. 4,516,194 shows a pen light comprising a hollow substantially cylindrical housing having a retainer member secured to the rear portion thereof to house a single voltage source in operative engagement with a light source, a first conductor member movable between a first and second position and a second conductor member each disposed within the hollow substantially cylindrical housing to operatively engage the light source and the voltage source respectively and an actuator clip attached to the hollow substantially cylindrical housing movable between a first and second position to selectively engage the first conductor member such that when the actuator clip is in the first position the first conductor member is separated from the second conductor member to form an open circuit and when the actuator clip is in the second position the actuator clip engages the first conductor member to move the first conductor member from the first position to second position whereby the first conductor member engages the second conductor member to close the circuit and activate the light source.

U.S. Pat. No. 4,616,660 teaches a variable alternating current output nerve locator/stimulator comprising a hollow substantially cylindrical enclosure configured to operatively house a direct current power source electrically coupled to a current power convertor including circuitry to convert the direct current to alternating current electrically coupled to a current regulator, a nerve probe electrically coupled to the current regulator and a ground electrically coupled to the direct current power source, a removable nerve probe cover and a removable ground cover removably attached to opposite ends of the hollow substantially cylindrical enclosure to permit selective withdrawal of the ground from the hollow substantially cylindrical enclosure and application of the nerve probe to the patient after adjustment of the current regulator to control the alternating current from the direct current power source.

U.S. Pat. No. 4,347,553 describes a reusable light comprising a housing configured to operatively retain a voltage source therein having an extended bulb assembly mounted on one end thereof and a switch pivotally mounted on the opposite end thereof, the extended bulb assembly comprises an elongated hollow sleeve having a mounting member attached on one end thereof to attach the extended bulb assembly to the housing and a bulb housing having a light source disposed therein attached to the opposite end thereof, a first conductor including a first and second conductor element extending substantially the length of the flexible light coupled to the light source, a second conductor disposed within the hollow sleeve being coupled to another portion of the light source and a removable cap to selectively house the extended bult assembly, the switch movable to operatively engage the first conductor means to selectively close the circuit and activate the light source.

Additional examples of the prior art are found in U.S. Pat. No. 2,994,324; U.S. Pat. No. 4,811,733; U.S. Pat. No. 4,903,696; U.S. Pat. No. 5,366,476; U.S. Pat. No. Des. 229,869; U.S. Pat. No. Des. 240,277; U.S. Pat. No. Des. 253,303 and U.S. Pat. No. Des. 254,150.

SUMMARY OF THE INVENTION

The present invention relates to a battery powered cautery assembly comprising a cautery and a removable safety cover.

The cautery comprises an outer housing having at least one battery disposed in the proximal end thereof, a cautery element attached to the distal end thereof with a conductor disposed therein to selectively couple the battery to the cautery element and a switch means movable between a first and second position hingedly attached thereto and disposed to selectively engage the conductor when in the second position to connect the cautery element to the battery.

The cautery element comprises an electrode support member to receive and support the distal end portions of a first electrode and a second electrode having a heading tip extending therebetween and an inner housing to house the proximal end portions of the first electrode and the second electrode and to operatively support a portion of the conductor thereon. The inner housing includes a substantially flat upper surface having an actuator aperture formed therethrough to permit electrical contact between the conductor and the first electrode when the switch means is in the second position.

The switch means comprises a switch actuator having a switch actuator retainer member formed on the distal end thereof hingedly attached to the outer housing by a hinge formed on the proximal end thereof.

The outer housing includes a substantially flat interior surface formed on the distal end portion thereof having a switch actuator aperture formed therethrough to operatively receive at least a portion of the switch actuator therein.

The substantially flat upper surface and the substantially flat interior surface cooperatively form an axial cautery alignment means to axially align the cautery element relative to the substantially cylindrical outer housing such that the switch actuator aperture and the actuator aperture are aligned in registry relative to each other.

The conductor comprises an elongated conductor strip or member including a first and second contact element formed on opposite ends thereof. A conductor alignment means is formed on the elongated conductive strip or member adjacent the first contact element aligns the conductor laterally and longitudinally relative to the switch actuator aperture formed on the outer housing and the actuator aperture formed in the substantially cylindrical inner housing such that the switch actuator, switch actuator aperture, first contact element, actuator aperture and first electrode are operatively aligned relative to each other.

The removable safety cover comprises a reduced distal portion and a an enlarged proximal portion having a groove or slot including peripheral edges formed on opposite sides thereof. The width of the groove or slot is greater than the width of the base of the switch actuator and less than the width of the top of the switch actuator such that when the removable safety cover is operatively mounted on the outer housing the peripheral edges are disposed on opposite sides of the base of the switch actuator between the top of the switch actuator and the exterior of the outer housing to prevent depression of the switch actuator to preclude inadvertent activation of the battery powered cautery assembly.

When in use, the removable safety cover is removed from the substantially cylindrical outer housing to permit actuation of the switch actuator by depression or movement from the first to second position such that the first contact element engages the first electrode completing the electrical circuit to selectively actuate the cautery element to heat the heating tip. The electrical circuit is completed since the second contact element engages the base or first terminal of the voltage source or battery and the second electrode engages the other or second terminal of the voltage source or battery.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which:

FIG. 1 is an exploded perspective view of the battery powered cautery assembly of the present invention.

FIG. 2 is a perspective view of the battery powered cautery assembly of the present invention.

FIG. 3 is a side view of the battery powered cautery of the present invention during assembly.

FIG. 4 is a cross-sectional side view of the battery powered cautery of the present invention.

FIG. 5 is a cross-sectional end view of the substantially cylindrical outer housing of the present invention taken along line 5—5 of FIG. 3.

FIG. 6 is an end view of the cautery element of the present invention taken along line 6—6 of FIG. 7.

FIG. 7 is a top view of the cautery element of the present invention.

FIG. 8 is a cross-sectional end view of the battery powered cautery assembly of the present invention taken along line 8—8 of FIG. 2.

Similar reference characters refer to similar parts throughout the several views of the drawings.

DETAILED DESCRIPTION OF THE PREFERRED EMBODIMENT

As shown in FIGS. 1 through 4, the present invention relates to a battery powered cautery assembly generally indicated as 10 comprising a cautery generally indicated as 12 and a removable safety cover generally indicated as 14.

As best shown in FIGS. 1 through 4, the cautery 12 comprises a substantially cylindrical outer housing 16 having at least one battery 18 disposed in the proximal end thereof, a cautery element generally indicated as 20 attached to the distal end thereof with a conductor generally indicated as 22 disposed therein to selectively couple the battery 18 to the cautery element 20 and a switch means generally indicated as 24 movable between a first and second position hingedly attached thereto and disposed to selectively engage the conductor 22 when in the second position to connect the cautery element 20 to the battery 16 as described more fully hereinafter.

As best shown in FIGS. 2 through 4, the cautery element 20 comprises a cautery heating holder 26 having a first electrode channel 28 and a second electrode channel 30 formed therethrough to receive and support the distal end portions of a first electrode 32 and a second electrode 34 respectively therein and a substantially cylindrical inner housing 36 to house the proximal end portions of the first electrode 32 and the second electrode 34 and to operatively support a portion of the conductor 22 thereon as described more fully hereinafter. The distal ends of the first electrode 32 and the second electrode 34 are operatively connected by a heating tip 38 extending outwardly therefrom. As best shown in FIGS. 3, 6 and 7, the substantially cylindrical inner housing 36 includes a substantially flat upper surface 40 having an actuator aperture 42 formed therethrough to permit electrical contact between the conductor 22 and the first electrode 32 when the switch means 24 is in the second position and a recess or keyway 44 formed on the proximal end of the substantially flat upper surface 40 to receive a portion of the conductor 22 therein.

As best shown in FIGS. 1 through 4 and 8, the switch means 24 comprises a switch actuator 46 having a switch actuator retainer member 48 formed on the distal end thereof hingedly attached to the substantially cylindrical outer housing 16 by a hinge 50 formed on the proximal end thereof.

As best shown in FIGS. 1 through 4, the substantially cylindrical outer housing 16 includes a substantially flat interior surface 52 formed on the distal end portion thereof having a switch actuator aperture 54 formed therethrough to operatively receive at least a portion of the switch actuator 46 therein. When the cautery 12 is operatively assembled the switch actuator retainer member 48 is disposed within the substantially cylindrical outer housing 16 adjacent the distal end of the switch actuator aperture 54.

The substantially flat upper surface 40 and the substantially flat interior surface 52 cooperatively form an axial cautery alignment means to axially align the cautery heating element 22 relative to the substantially cylindrical outer housing 16 such that the switch actuator aperture 54 and the actuator aperture 42 are aligned in registry relative to each other when the distal end of the substantially cylindrical inner housing 36 engages a first retainer flange 56 formed on the distal end of the substantially cylindrical outer housing 16 having an aperture 58 formed therein to receive the electrode support member 26 therethrough. A second retainer flange 60 is formed on the proximal end of the substantially cylindrical outer housing 16 to retain a retention member or disc 62 and a bias 64 within the substantially cylindrical outer housing 16 to maintain a portion of the conductor 22 in operative engagement with the battery 18.

As best shown in FIGS. 3 and 4, the conductor 22 comprises an elongated conductor strip or member 66 including a first and second contact point or element indicated as 68 and 70 respectively formed on opposite ends thereof. A conductor alignment means comprising a conductor alignment element generally indicated as 72 is formed on the elongated conductive strip or member 66 adjacent the first contact element 68 and the recess or keyway 44 aligns the conductor 22 laterally and longitudinally relative to the switch actuator aperture 54 formed on the substantially cylindrical outer housing 16 and the actuator aperture 42 formed in the substantially cylindrical inner housing 36 such that the switch actuator 46, switch actuator aperture 54, first contact element 68, actuator aperture 42 and first electrode 32 are operatively aligned relative to each other.

As shown, the conductor alignment element 72 may comprise a pair of alignment members or legs each indicated as 73 extending downwardly from the elongated conductive strip or member 66 and spaced relative to each other to be disposed on opposite ends of the recess or keyway 44.

As shown in FIGS. 1, 2 and 8, the removable safety cover 14 comprises a substantially cylindrical reduced distal portion 74 and a substantially cylindrical enlarged proximal portion 76 having a groove or slot 78 including peripheral edges 80 formed on opposite sides thereof. The width of the groove or slot 78 is greater than the width of the base 82 of the switch actuator 46 and less than the width of the top 84 of the switch actuator 46 such that when the removable safety cover 14 is operatively mounted on the substantially cylindrical outer housing 16 the peripheral edges 80 are disposed on opposite sides of the base 82 of the switch actuator 46 between the top 84 of the switch actuator 16 and the exterior of the substantially cylindrical outer housing 16 to prevent depression of the switch actuator 46 to preclude inadvertant activation of the battery powered cautery assembly 10.

When in use, the removable safety cover 14 is removed from the substantially cylindrical outer housing 16 to permit actuation of the switch actuator 24 by depression or movement from the first to second position such that the first contact element 68 engages the first electrode 32 completing the electrical circuit to selectively heat the heating tip 38. The electrical circuit is completed since the second contact element 70 engages the base or first terminal of the voltage source or battery 18 and the second electrode 34 engages the other or second terminal of the voltage source or battery 18.

Although a battery powered cautery assembly 10 has been discussed, the invention can be equally practical with a pen light, nerve locator/stimulator or other handheld battery powered device.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described.

What is claimed is:

1. A battery operated cautery comprising an outer housing having a switch actuator aperture including a distal end and a proximal end formed therein and configured to retain a battery voltage source including a first terminal and a second terminal, said outer enclosure having a distal end portion and a proximal end portion, a cautery element mounted on said distal end portion of said outer housing, a conductor including a first contact element movable between a first position and a second position formed on one end thereof and a second contact element formed on the opposite end thereof, said conductor being operatively housed within said outer housing, a switch actuator having a proximal end and a distal end hingedly attached to said outer housing and movable between a first position and a second position and at least partially disposed within said switch actuator aperture, said switch actuator being disposed adjacent said first contact element, said cautery element comprises a cautery heating holder supporting a first electrode and a second electrode at least partially disposed within said outer housing and cooperatively supporting a heating tip extending outwardly from said outer housing, said first electrode and said second electrode each including a distal end portion and a proximal end portion, said first contact element being normally biased in said first position in spaced relation relative to said first electrode, said second electrode being adapted to be electrically connected to said second terminal of said battery voltage source such that said first contact element is moved from said first position to said second position by depression of said switch actuator to engage said first electrode to complete the electrical circuit thereto to actuate said battery operated cautery, said cautery heating holder comprises an electrode support member to support said first electrode and said second electrode and an inner housing to house said proximal end portions of said first electrode and said second electrode and to operatively support a portion of said conductor thereon.

2. The battery operated cautery of claim 1 further including a removable safety cover to selectively cover said heating tip, said removable safety cover including a proximal portion insertable between said outer housing and a portion of said switch actuator when said removable safety cover is mounted on said outer housing to lock said switch actuator in said first position to prevent actuation of said heating tip.

3. The battery operated cautery of claim 1 further including an axial cautery alignment means to axially align said cautery element relative to said switch actuator aperture.

4. The battery operated cautery of claim 3 wherein said axial cautery alignment means comprises a substantially flat upper surface having a proximal end and a distal end formed on said inner housing and a substantially flat interior surface formed on the distal end portion of said outer housing.

5. The battery operated cautery of claim 1 wherein said inner housing further includes an actuator aperture formed therethrough to permit electrical contact between said conductor and said first electrode when said switch actuator is in said second position.

6. The battery operated cautery of claim 5 wherein said battery operated cautery further includes a conductor alignment means to align said conductor relative to said switch actuator, said switch actuator aperture, said actuator aperture and said first electrode.

7. The battery operated cautery of claim 6 wherein said conductor alignment means comprising a conductor alignment element formed on said conductor adjacent said first contact element and a keyway formed on said inner housing to align said conductor laterally and longitudinally relative to said switch actuator aperture formed on said outer housing and said actuator aperture formed in said inner housing such that said switch actuator, said switch actuator aperture, said first contact element, said actuator aperture and said first electrode are operatively aligned relative to each other.

8. The battery operated cautery of claim 1 wherein said battery operated cautery further includes a conductor alignment means to align said conductor relative to said switch actuator, said switch actuator aperture and said first electrode.

9. The battery operated cautery of claim 8 wherein said conductor alignment means comprising a conductor alignment element formed on said conductor adjacent said first contact element and a keyway formed on said inner housing to align said conductor laterally and longitudinally relative to said switch actuator aperture formed on said outer housing and said actuator aperture formed in said inner housing such that said switch actuator, said switch actuator aperture, said first contact element, said actuator aperture and said first electrode are operatively aligned relative to each other.

10. The battery operated cautery of claim 1 wherein said switch actuator includes a switch actuator retainer member formed on said distal end thereof to engage said outer housing adjacent said distal end of said switch actuator aperture to normally maintain said switch actuator in said first position and said switch actuator is hingedly attached to said outer housing by a hinge formed on said proximal end of said switch actuator.

11. The battery operated cautery of claim 1 wherein said switch actuator includes a switch actuator retainer member formed on said distal end thereof to engage said outer housing adjacent said distal end of said switch actuator aperture to normally maintain said switch actuator in said first position.

12. The battery operated cautery of claim 11 wherein said switch actuator is hingedly attached to said outer housing by a hinge formed on said proximal end of said switch actuator.

13. A handheld battery powered device comprising an outer housing having a switch actuator aperture including a distal end and a proximal end formed therein and configured to retain a battery voltage source including a first terminal and a second terminal, said outer housing having a distal end portion and a proximal end portion, a working implement mounted on said distal end portion of said outer housing, a conductor including a first contact element movable between a first position and a second position formed on one end thereof and a second contact element formed on the opposite end thereof, said conductor being operatively housed within said outer housing, a switch actuator having a proximal end and a distal end hingedly attached to said outer housing and movable between a first position and a second position and at least partially disposed within said switch actuator aperture, said switch actuator being disposed adjacent said first contact element, said working implement comprising a first electrode and a second electrode at least partially disposed within said outer housing and cooperatively supporting a work piece extending outwardly from said outer housing, said first electrode and second electrode each including a distal end portion and a proximal end portion said first contact element being normally biased in said first position in spaced relation relative to said first electrode, said second electrode being adapted to be electrically connected to said second terminal of said battery voltage source such that said first contact element is moved from said first position to said second position by depression of said switch actuator to engage said first electrode to complete the electrical circuit thereto to actuate said handheld battery powered device, said working implement further comprises an electrode support member to support said first electrode and said second electrode and an inner housing to house the proximal end portions of said first electrode and said second electrode to operatively support a portion of said conductor thereon.

14. The handheld battery powered device of claim 13 further including an axial cautery alignment means to axially align said working implement relative to said switch actuator aperture.

15. The handheld battery powered device of claim 14 wherein said axial cautery alignment means comprises a substantially flat upper surface having a proximal end and a distal end formed on said inner housing and a substantially flat interior surface formed on the distal end portion of said outer housing.

16. The handheld battery powered device of claim 13 wherein said inner housing further includes an actuator aperture formed therethrough to permit electrical contact between said conductor and said first electrode.

17. The handheld battery powered device of claim 16 wherein said handheld battery powered device further includes a conductor alignment means to align said conductor relative to said switch actuator, said switch actuator aperture, said actuator aperture and said first electrode.

18. The handheld battery powered device of claim 17 wherein said conductor alignment means comprising a conductor alignment element formed on said conductor adjacent said first contact element and a keyway formed on said inner housing to align said conductor laterally and longitudinally relative to said switch actuator aperture formed on said outer housing and said actuator aperture formed in said inner housing such that said switch actuator, said switch actuator aperture, said first contact element, said actuator aperture and said first electrode are operatively aligned relative to each other.

19. The handheld battery powered device of claim 13 wherein said handheld battery powered device further includes a conductor alignment means to align said conductor relative to said switch actuator, said switch actuator aperture and said first electrode.

20. The battery operated cautery of claim 19 wherein said conductor alignment means comprises a conductor alignment element formed on said conductor adjacent said first contact element and a keyway formed on said inner housing to align said conductor laterally and longitudinally relative to said switch actuator aperture formed on said outer housing and said actuator aperture formed in said inner housing such that said switch actuator, said switch actuator aperture, said first contact element, said actuator aperture and said first electrode are operatively aligned relative to each other.

21. The handheld battery powered device of claim 13 further including a removable safety cover to selectively cover said workpiece, said removable safety cover including a proximal portion insertable between said outer housing and a portion of said switch actuator when said removable safety cover is mounted on said outer housing to lock said switch actuator in said first position to prevent actuation of said workpiece.

22. The handheld battery powered device of claim 13 wherein said switch actuator includes a switch actuator retainer member formed on said distal end thereof to engage said outer housing adjacent said distal end of said switch actuator aperture to normally maintain said switch actuator in said first position and said switch actuator is hingedly attached to said outer housing by a hinge formed on said proximal end of said switch actuator.

23. The handheld battery powered device of claim 13 wherein said switch actuator is hingedly attached to said outer housing by a hinge formed on said proximal end of said switch actuator.

* * * * *